(12) United States Patent
Mei et al.

(10) Patent No.: US 9,130,171 B2
(45) Date of Patent: Sep. 8, 2015

(54) HIGH-MOBILITY STRUCTURES, APPARATUSES AND METHODS THEREFOR

(71) Applicant: The Board of Trustees of the Leland Stanford Junior University, Palo Alto, CA (US)

(72) Inventors: Jianguo Mei, Greensboro, NC (US); Zhenan Bao, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 144 days.

(21) Appl. No.: 13/680,746

(22) Filed: Nov. 19, 2012

(65) Prior Publication Data
US 2013/0126836 A1    May 23, 2013

Related U.S. Application Data

(60) Provisional application No. 61/561,632, filed on Nov. 18, 2011.

(51) Int. Cl.
| | |
|---|---|
| *H01L 51/00* | (2006.01) |
| *C08F 34/04* | (2006.01) |
| *C08G 69/48* | (2006.01) |
| *H01B 1/12* | (2006.01) |
| *C07F 7/08* | (2006.01) |
| *H01L 51/10* | (2006.01) |
| *C08G 61/12* | (2006.01) |
| *C08G 77/42* | (2006.01) |
| *C08G 61/10* | (2006.01) |
| *H01L 51/05* | (2006.01) |

(52) U.S. Cl.
CPC .......... *H01L 51/0036* (2013.01); *C07F 7/0849* (2013.01); *C07F 7/0852* (2013.01); *C08F 34/04* (2013.01); *C08G 61/10* (2013.01); *C08G 61/124* (2013.01); *C08G 61/126* (2013.01); *C08G 69/48* (2013.01); *C08G 77/42* (2013.01); *H01B 1/127* (2013.01); *H01L 51/0043* (2013.01); *H01L 51/0094* (2013.01); *H01L 51/10* (2013.01); *C08G 2261/144* (2013.01); *C08G 2261/3223* (2013.01); *C08G 2261/3241* (2013.01); *C08G 2261/3243* (2013.01); *H01L 51/0053* (2013.01); *H01L 51/0545* (2013.01); *H01L 51/0558* (2013.01)

(58) Field of Classification Search
None
See application file for complete search history.

(56) References Cited

U.S. PATENT DOCUMENTS 5,945,502 A * 8/1999 Hsieh et al. ............... 528/101
6,495,644 B1 * 12/2002 Chen et al. ............... 526/258

OTHER PUBLICATIONS

"Boosting the Ambipolar Performance of Solution-Processable Polymer Semiconductors via Hybrid Side-Chain Engineering" authored by Lee et al. and published in JACS (2013)135, 9540-47.*

Mark, J., "Some Interesting Things about Polysiloxanes." Acc. Chem. Res., vol. 37, pp. 946-953, (2004).

Dantlgraber, G.; Eremin, A.; Diele, S.; Hauser, A.; Kresse, H.; Pelzl, G. and Tschierske, C., "Chirality and Macroscopic Polar Order in a Ferroelectric Smectic Liquid-Crystalline Phase Formed by Achiral Polyphilic Bent-Core Molecules." Angew. Chem. Int. Ed., vol. 41, No. 13, (2002).

Zhou, H.; Yang, L; Stuart, A. C.; Price, S. C.; Liu, S. and You, W., "Development of Fluorinated Benzothiadiazole as a Structural Unit for a Polymer Solar Cell of 7% Efficiency." Angew. Chem. Int. Ed., vol. 50, pp. 2995-2998, (2011).

Bredas, J.-L.; Beljonne, D.; Coropceanu, V. and Cornl, J., "Charge-Transfer and Energy-Transfer Processes in Conjugated Oligomers and Polymers: A Molecular Picture." Chem. Rev., vol. 104, pp. 4971-5003, (2004).

Grimsdale, A. C.; Chan, K. L; Martin, R. E.; Jokisz, P. G. and Holmes, A. B., "Synthesis of Light-Emitting Conjugated Polymers for Applications in Electroluminescent Devices." Chem. Rev., vol. 109, pp. 897-1091, (2009).

Carsten, B.; He, F.; Son, H. J.; Xu, T. and Yu, L., "Stille Polycondensation for Synthesis of Functional Materials." Chem. Rev. vol. 111, pp. 1493-1528, (2011).

Zhang, W; Smith, J.; Watkins, S. E.; Gysel, R.; McGehee, M.; Salleo, A.; Kirkpatrick, J.; Ashraf, S.; Anthoupoulos, T.; Heeney, M. and McCulloch, I., "Indacemodithiophene Semiconducting Polymers for High-Performance, Air-Stable Transistors." J. Am. Chem. Soc., vol. 132, pp. 11437-11439, (2010).

Son, H. J.; Wang, W.; Xu, T.; Liang, Y.; Wu, Y; Li, G. and Yu, L.,"Synthesis of Fluorinated Polythienothiophene-co-benzodithiophenes and Effect of Fluorination on the Photovoltaic Properties." J. Am. Chem. Soc. vol. 133, pp. 1885-1894, (2011).

Li, Y.; Sonar, P.; Singh, S. P.; Soh, M. S.; van Meurs, M. and Tan, J., "Annealing-Free High-Mobility Diketopyrrolopyrrole-Quaterthiophene Copolymer for Solution-Processed Organic Think Film Transistors." J. Am. Chem. Soc. vol. 133, pp. 2198-2204, (2011).

(Continued)

*Primary Examiner* — Marc Zimmer
(74) *Attorney, Agent, or Firm* — Crawford Maunu PLLC (57) ABSTRACT

Various apparatuses, systems and methods involve high mobility materials. In accordance with one or more example embodiments, a material includes a conjugated molecule and a side chain bonded to the conjugated molecule. The side chain includes at least one of a siloxane-terminated unit and a derivative of a siloxane-terminated unit that enhance solubility of the conjugated molecule. Further, the side chain facilitates a π-stacking distance between the conjugated molecules when stacked (e.g., in an organic semiconductor film), thereby facilitating carrier mobility between the conjugated molecules.

22 Claims, 6 Drawing Sheets

(56) References Cited

OTHER PUBLICATIONS

Tsao, H. N.; Cho, D. M.; Park, L; Hansen, M. R.; Mavrinskiy, A.; Yoon, D. Y.; Graf, R.; Pisula, W.; Spiess, H. W. and Mullen, K., "Ultrahigh Mobility in Polymer Field-Effect Transistors by Design." J. Am. Chem. Soc. vol. 133, pp. 2605-2612, (2011).

Bronstein, H.; Chen, S.; Ashraf, R. S.; Zhang, W.; Du, J.; Durrant, J. R.; Tuladhar, P. S.; Song, K.; Watkins, S. E.; Geerts, Y.; Wienk, M. M.; Janssen, R. A.; Anthopoulos, T.; Sirringhaus, H.; Heeney, M. and McCulloch, I., "THieno[3,2-b]thiophene-Diketopyrrolopyrrole-Containing Polymers for High-Performance Organic Field-Effect Transistors and Organic Photovoltaic Devices." J. Am. Chem. Soc., vol. 133, pp. 3272-3275, (2011).

He, F.; Wang, W.; Chen, W.; Xu, T.; Darling, S. B.; Strzalka, J.; Liu, Y. and Yu L., "Tetrathienoanthracene-Based Copolymers for Efficient Solar Cells." J. Am. Chem. Soc. vol. 133, pp. 3284-3287, (2011).

Lei, T.; Cao, Y.; Fan, Y.; Liu, C.-J.; Yuan, S.-C. and Pei, J., "High-Performance Air-Stable Organic Field-Effect Transistors: Isoindigo-Based Conjugated Polymers." J. Am. Chem. Soc. vol. 133, pp. 6099-6101, (2011).

Wang, E.; Ma, Z.; Zhang, Z.; Vandewal, K.; Henriksson, P.; Inganas, O.; Shang, F. and Andersson, M. R., "An Easily Accessible Isoindigo-Based Polymer for High-Performance Polymer Solar Cells." J. Am. Chem. Soc. vol. 133, pp. 14244-14247, (2011).

Zhang, X.; Richter, L. J.; DeLongchamp, D. M.; Kline, R. J.; Hammond, M. R.; McCulloch, I.; Heeney, M.; Ashraf, R. S.; Smith, J.N.; Anthopoulos, T.D.; Schroeder, B.; Geerts, Y. H.; Fischer, D. A. and Toney, M. F., "Molecular Packing of High-Mobility Diketo Pyrrolo—Pyrrolo Polymer Semiconductors with Branched Alkyl Side Chains." J. Am. Chem. Soc. vol. 133, pp. 15073-15084, (2011).

Mei, J.; Graham, K. R.; Stalder, R. and Reynolds, J. R., "Synthesis of Isoindigo-Based Oligothiophenes for Molecular Bulk Heterojunction Solar Cells." Organic Letters, vol. 12, No. 4, pp. 660-663, (2010).

Rivnay, J.; Noriega, R.; Kline, R. J.; Sallio, A. and Toney, M. F., "Quantitative Analysis of Lattice Disorder and Crystallite Size Organic Semiconductor Thin Films." Physical Review B 84, 045203, (2011).

Mei, J.; Kim, D. H.; Ayzner, A. L.; Toney, M. F. and Bao, Z., "Siloxane-Terminated Solubilizing Side Chains: Bringing Conjugated Polymer Backbones Closer and Boosting Hole Mobilities in Thin-Film Transistors." J. Am. Chem. Soc. vol. 133, pp. 20130-20133, (2011).

Zhang, M.; Tsao, H. N.; Pisula, W.; Yang, C.; Mishra, A. K. and Müllen, K., "Field-Effect Transistors Based on a Benzothiadiazole-Cyclopentadithiophene Copolymer," J. Am. Chem. Soc., 129, pp. 3472-3473, (2007).

Cheng, Y.-J.; Yang, S.-H. and Hsu, C.-S., "Synthesis of Conjugated Ploymers for Organic Solar Cell Applications," Chemical Reviews, 109, pp. 5868-5923, (2009).

Ito, Y.; Virkar, A. A.; Mannsfeld, S.; Oh, J. H.; Toney, M.; Locklin, J. and Bao, Z., "Crystalline Ultrasmooth Self-Assembled Monolayers of Alkylsilanes for Organic Filed-Effect Transistors," J. Am. Chem. Soc., 131, pp. 9396-9404, (2009).

Piliego, C.; Holcombe, T. W.; Douglas, J. D.; Woo, C. H.; Beaujuge, P. M. and Fréchet, J. M. J., "Synthetic Control of Structural Order in N-Alkylthieno[3,4-c]pyrrole-4,6-dione-Based Polymers for Efficient Solar Cells," J. Am. Chem. Soc., 132, pp. 7595-7597, (2010).

Varotto, A.; Treat, N. D.; Jo, J.; Shuttle, C. G.; Batara, N. A.; Brunetti, F. G.; Seo, J. H.; Chabinyc, M. L.; Hawker, C. J.; Heeger, A. J. and Wudl, F., "1,4-Fullerene Derivatives: Tuning the Properties of the Electron Transporting Layer in Bulk-Heterojunction Solar Cells," Angew. Chem. Int. Ed., 50, pp. 5166-5169, (2011).

Amb, C. M.; Chen, S.; Graham, K. R.; Subbiah, J.; Small, C. E.; So, F. and Reynolds, J. R., "Dithienogermole as a Fused Electron Donor in Bulk Heterojunction Solar Cells", J. Am. Chem. Soc., 133, pp. 10062-10065, (2011).

Rivnay, J.; Steyrleuthner, R.; Jimison, L. H.; Casadei, A.; Chen, Z.; Toney, M. F.; Facchetti, A.; Neher, D. and Salleo, A., "Drastic Control of Texture in a High Performance n-Type Polymeric Semiconductor and Implications for Charge Transport", Macromolecules, 44, pp. 5246-5255, (2011).

Hu, et al. "Core-Expanded Naphthalene Diimides Fused with Sulfur Heterocycles and End-Capped with Electron-Withdrawing Groups for Air-Stable Solution-Processed n-Channel Organic Thin Film Transistors," dx.doi.org/10.1021/cm102850j, Chem. Mater. 2011, 23, 1204-1215.

* cited by examiner

HIGH-MOBILITY STRUCTURES, APPARATUSES AND METHODS THEREFOR

BACKGROUND

Solution processability is one of the most distinctive features that set organic semiconducting materials apart from their inorganic counterparts, such as silicon-based semiconductors. This property makes conjugated polymers attractive for applications such as low-cost solar cells and field-effect transistors, owing to their compatibility with widely-used fast printing techniques. Solubility of conjugated polymers in common organic solvents (e.g., chloroform, toluene and chlorobenzene) can result from the attachment of flexible aliphatic chains as solubilizing groups onto conjugated moieties. Such solubilizing groups may include, for example, branched alkyl chains such as 2-ethylhexyl, 2-hexyldecyl and 2-octyldodecyl groups and linear alkyl chains such as hexyl, octyl and dodecyl groups.

While such materials have been useful in a variety of applications, their implementation can be difficult with respect to achieving high mobilities. These and other matters have presented challenges to the implementation of materials, such as polymer-based materials, for a variety of applications.

SUMMARY

Various example embodiments are directed to conjugated structures with high mobility, and their implementation, and to addressing one or more of the challenges such as discussed above.

According to an example embodiment, a side chain material includes at least one of a siloxane-terminated unit and a derivative of a siloxane-terminated unit configured and arranged to enhance solubility of the conjugated molecule. In a more particular embodiment, the side chain is bonded to the conjugated molecules, and used to enhance solubility of the conjugated molecule. The side chain further sets a π-stacking distance between the conjugated molecules that facilitates carrier mobility between the conjugated molecules (e.g., higher carrier mobility, relative to other side chains and/or approaches to solubilizing the conjugated molecules, such as for manufacturing organic semiconductor devices).

In accordance with another embodiment, an apparatus includes first and second conductive terminals and an organic semiconductor film electrically coupled to pass carriers between the conductive terminals. The organic semiconductor film includes a plurality of conjugated molecules and, for each of the conjugated molecules, a side chain bonded to the conjugated molecule. The side chain includes at least one of a siloxane-terminated unit and a derivative of a siloxane-terminated unit that enhance solubility of the conjugated molecule, and that further operate with the conjugated molecule to set a desirable π-stacking distance between the conjugated molecules in the organic semiconductor film. With this approach, a relatively shorter π-stacking distance can be set to facilitate/enhance carrier mobility between the conjugated molecules (e.g., relative to other solubilizing side chains).

Other embodiments are directed to methods involving a solubilizing side chain as discussed above. In one embodiment, solubilizing side chains are bonded to conjugated molecules, with each side chain having at least one of a siloxane-terminated unit and a derivative of a siloxane-terminated unit. A solution is formed in a solvent, using the solubilizing side chains to increase solubility of the conjugated molecules.

The above discussion/summary is not intended to describe each embodiment or every implementation of the present disclosure. The figures and detailed description that follow also exemplify various embodiments.

DESCRIPTION OF THE FIGURES

Various example embodiments may be more completely understood in consideration of the following detailed description in connection with the accompanying drawings, in which.

While various embodiments discussed herein are amenable to modifications and alternative forms, aspects thereof have been shown by way of example in the drawings and will be described in detail. It should be understood, however, that the intention is not to limit the invention to the particular embodiments described. On the contrary, the intention is to cover all modifications, equivalents, and alternatives falling within the scope of the disclosure including aspects defined in the claims.

DETAILED DESCRIPTION

Aspects of the present disclosure have application and are directed to materials and apparatuses for conjugated molecules (e.g., polymer, oligomer or other small molecule-based materials), and to side chains with such apparatuses and methods, such as used in connection with thin-film transistors and other circuit applications.

As consistent with one or more embodiments, a conjugated molecule (e.g., a polymer and/or oligomer, or another small molecule) is coupled with a solubilizing sidechain in molecular structures exhibiting high-mobility charge carriers, such as polymer-based, oligomer-based or other small-molecule-based conjugated structures with a side chain material that facilitates such mobility (e.g., in thin-film applications). In some embodiments, a siloxane-terminated or siloxaine-derivative solubilizing group is used as a side chain in a conjugated polymer. Various implementations involve crystallites having relatively π-π distances, in which such side chains are used to enhance mobility.

One or more embodiments are directed to a solubilizing side chain material having a linear aliphatic chain and a siloxane-terminated unit. Other embodiments are directed to a material, including conjugated molecules and, for each conjugated molecule, one or more side chains (e.g., as described above) bonded to the conjugated molecule. Each side chain includes at least one of a siloxane-terminated unit and a derivative of a siloxane-terminated unit, which enhance solubility of the conjugated molecule and set π-stacking distance between the conjugated molecules that facilitates carrier mobility. In these contexts, the term solubilizing refers to rendering a material more soluble in one or more solvents.

In some embodiments, the conjugated molecules are stacked in an organic semiconductor film having a carrier mobility set via the π-stacking distance, with a branching distance of the side chain, relative to the conjugated molecule, setting the π-stacking distance. For instance, in some implementations, such a side chain includes a linear spacer that couples/bonds at least one of the siloxane-terminated unit and the derivative of the siloxane-terminated unit to the conjugated molecule. These approaches can facilitate π-stacking distance between the conjugated molecules that is shorter than a π-stacking distance of at least one of highly-branched ethylhexyl and highly-branched hexyldecyl. As implemented herein, such π-stacking distance between the conjugated molecules can be set to less than 3.7 Angstroms, or less than 3.6 Angstroms, to suit various embodiments. Using these approaches, the resulting structure can be formed in an organic semiconductor film having a carrier mobility of one of at least 0.5 $cm^2V^{-1}s^{-1}$, and at least 2.00 $cm^2V^{-1}s^{-1}$. In some implementations, the side chain operates to crosslink to form the film including the conjugated molecule, from solution (e.g., in a solvent, which may be part of a material including the conjugated molecule and side chain, in accordance with one or more embodiments).

In some embodiments, a crystalline coherence length is increased for one or more molecular structures, to lower the density of parasitic grain boundaries in the structure. In some implementations, this approach is carried out using semicrystalline conjugated polymer films (e.g., polycrystalline), in which charges hop across grain boundaries as they traverse the macroscopic conduction channel length. In other implementations, texture differences are used for contributing to the mobility differences. In certain embodiments, average FET hole mobility of 2.00 $cm^2V^{-1}s^{-1}$ is achieved for an isoindigo-based polymer (e.g., in comparison to 0.30 $cm^2V^{-1}s^{-1}$ for a reference polymer). Such approaches can be implemented using siloxane-terminated solubilizing groups extendable to other conjugated systems, such as diketopyrrolopyrrole-based conjugated polymers.

Various embodiments are directed to a siloxane-terminated solubilizing group, and one or more applications thereof, such as those involving a side chain in an isoindigo-based conjugated polymer. In particular experiments and/or detailed implementations, such a polymer exhibits a π-π stacking distance of about 3.58 Angstrom, average hole mobility of 2.00 $cm^2V^{-1}s^{-1}$, and a hole mobility up to about 2.48 $cm^2V^{-1}s^{-1}$ with solution-processed thin-film transistors.

These and other approaches may be implemented with one or more of a variety of apparatuses, such as electronic devices, field-effect transistors, organic solar cells, memory devices, organic light-emitting devices, organic transistor sensors, chemical sensors, biological sensors, pressure sensors, and doped conductors. One or more of these apparatuses may be implemented in a flexible or stretchable context, as facilitated via the polymer materials used therein. Certain implementations use other types of siloxane to functionalize side chains and extend the side chains to conjugated materials for a variety of applications.

A more particular embodiment is directed to a material including a block of linear alkyl chain and a flexible 1,1,1,3,5,5,5-heptamethyltrisiloxane terminal unit. The Si—O bond length is about 1.64 Å, which is significantly longer than C—C bond length of 1.53 Å, and the Si—O—Si bond angle of 143 degrees is also significantly larger than the usual tetrahedral angle (~110 degrees). Using a siloxane block as part of a solubilizing chain, solubility is facilitated in the resulting conjugated polymers (e.g., isoindigo-based conjugated polymers), and the site at which the side chain branches is moved away from the conjugated backbone to facilitate charge transfer via close stacking of the backbones. In some implementations, the siloxane group also functions as a crosslinking site. The linear alkyl chain serves as a spacer to fine tune solubility and to control the distance between the conjugated building blocks and the very bulky siloxane group.

Polymer backbones and related side chains as described herein may be manufactured using one or more of a variety of approaches, to suit particular embodiments. In some embodiments, a target polymer is manufactured using 2,6-dibromoisoindigo, and an alkeneterminated linear alkyl chain is attached to an isoindigo core via base-promoted N-alkylation. Hydrosilylation of terminal alkene with 1,1,1,3,5,5,5-heptamethyltrisiloxane is effected in the presence of a catalyst, yielding highly soluble isoindigo monomer with siloxane-terminated solubilizing chains, under microwave conditions. The polymer is purified by precipitation into acetone followed by Soxhlet extraction using acetone, hexane and chloroform. Absorption characteristics include an absorption maximum at about 728 nm and a shoulder at about 662 nm. A planar-type backbone can be achieved, by mitigating/minimizing steric repulsion between sidechains. The absorption of the resulting material in a film arrangement undergoes a shift to a shorter wavelength (~16 nm), relative to in solution. A HOMO (highest occupied molecular orbital) level of about −5.20 eV and LUMO (lowest unoccupied molecular orbital) value of about −3.58 eV can be achieved.

The polymer-based materials as discussed herein may be implemented with a variety of apparatuses, for a variety of applications. In some embodiments, bottom-gate/top-contact field-effect transistors (OFETs) are formed using a conjugated backbone and sidechain as discussed herein over an underlying substrate, as an active region between source/drain electrodes (e.g., Au electrodes (W=1000 μm, L=50 μm)). In some implementations, the active region is formed on an $SiO_2$ dielectric that is on a heavily n-doped Silicon wafer, with the dielectric surface modified with a dense crystalline octadecyltrimethoxysilane (OTMS) self-assembled monolayer. For instance, a solution including the conjugated polymer/solubilizing side chain material can be spin-coated as a solution in chloroform (4 mg/ml) at a speed of 1000 rpm for 60 s to achieve a film thickness of about 75-83 nm, followed by annealing (e.g., 170° C. for 1 hr) to achieve a mobility of about 0.33±0.14 cm2V-1s-1, maintaining an on/off current ratio of 105. In other embodiments, films can be implemented with a mobility of about 1.78 (±0.35) cm2V-1s-1 (150° C. anneal), about 2.0 (±0.49) cm2V-1s-1 (170° C. anneal), and about 2.48 cm2V-1s-1 under other anneal conditions. Such devices can be implemented with high stability against atmospheric oxygen, and with mitigated degradation in mobility over time (e.g., when films are stored under ambient conditions).

The mobility characteristics as described herein may be facilitated using various approaches, such as those involving close stacking and described above (e.g., using strong polymer intermolecular interactions in the solid-state). In some implementations, donor-acceptor type polymers are used to form interchain aggregates by virtue of strong π-π stacking, which leads to efficient charge transport in devices. Such π-stacking planes can be oriented largely perpendicular to the substrate (the π tacking is in-plane), to facilitate mobility. For instance, a π-stacking distance of about 3.58 Å can be obtained, with a crystalline coherence length of in-plane π-stacking Bragg reflection being about 138 Å (e.g., as related to both the total number of scattering lattice plains in a given crystallite as well as the degree of crystalline disorder). As consistent with these approaches and recognition/discovery therein (and in one or more embodiments), a larger crystalline coherence length is used to facilitate a lower density of parasitic grain boundaries (which charges must hop across as they traverse the macroscopic conduction channel), and therein facilitating mobility. It has also been recognized/discovered that texture differences can facilitate mobility via in-plane transport with conjugated polymers in which holes and electrons move along the π-stacking direction, as facilitated by implementing orientation between grains. Accordingly, it has been discovered that, by setting one or more of a relative π-stacking distance, crystallographic orientation and crystalline coherence length, carrier mobilities within the organic semiconductor film of at least $0.5\ cm^2V^{-1}s^{-1}$, and at least $2.00\ cm^2V^{-1}s^{-1}$ can be achieved.

For information regarding details of other embodiments, experiments and applications that can be combined in varying degrees with the teachings herein, reference may be made to the teachings and underlying references provided in the provisional patent application to which benefit is claimed, and which includes and Appendix entitled "*Siloxane-Terminated Solubilizing Sidechains Bringing conjugated Polymer backbones Closer and Boosting hole Mobilities in Thin-film Transistors*" as part of the provisional patent application, as well as the correspondingly-entitled publication and the Supporting Information document therewith (see Mei, et al., J. Am. Chem. Soc., 2011, 133 (50), pp. 20130-20133). In addition, for further information regarding implementations and applications to which one or more example embodiments of the present invention may be applied, reference may be made to one or more of the references cited in the Appendix (e.g., which aspects and embodiments may be implemented to form and/or implement polymer materials in a variety of devices). Each of these cited references is fully incorporated herein by reference.

Another embodiment is directed to an apparatus having first and second conductive terminals and an organic semiconductor film electrically coupled to pass carriers between the conductive terminals. The film includes a plurality of conjugated molecules and, for each of the conjugated molecules, one or more side chains bonded to the conjugated molecule. Each side chain includes at least one of a siloxane-terminated unit and a derivative of a siloxane-terminated unit that enhance the solubility of the conjugated molecule and that further set a π-stacking distance between the conjugated molecules in the organic semiconductor film upon formation from solution. Using this approach, carrier mobility between the conjugated molecules is enhanced. In various embodiments, the solubilizing side chain and the conjugated molecules are configured and arranged with a relative π-stacking distance, crystallographic orientation and crystalline coherence length that provide a carrier mobility within the organic semiconductor film of at least $2\ cm^2V^{-1}s^{-1}$.

The side chains as described above and otherwise herein may include one or more of a variety of materials, to suit particular applications. In some embodiments, the side chain includes a linear spacer bonded to the conjugated molecule. The resulting structure exhibits bond angles and a branch site offset of the side chain (relative to the conjugated molecule) that set the π-stacking distance (e.g., less than 3.6 Angstroms) between the conjugated molecules in the film. Using these approaches, a carrier mobility in the resulting organic semiconductor film can be at least $0.5\ cm^2V^{-1}s^{-1}$, or at least $2.00\ cm^2V^{-1}s^{-1}$ (e.g., using different manufacturing processes such as those involving annealing).

Various embodiments are directed to a method involving a side chain and conjugated polymer as described herein. In one embodiment, side chains are bonded to conjugated molecules, with each side chain including at least one of a siloxane-terminated unit and a derivative of a siloxane-terminated unit. A solution is formed in a solvent by using the solubilizing side chains to increase solubility of the conjugated molecules in the solvent.

In more particular embodiments, the solution is used to form an organic semiconductor film of the conjugated molecules having the solubilizing side chains bonded thereto. The solubilizing side chains are used to set a π-stacking distance between the conjugated molecules that facilitates carrier mobility between the conjugated molecules in the organic semiconductor film. In some instances, each side chain includes a linear spacer that is bonded to the conjugated molecule and exhibits bond angles and a branch site offset that set the π-stacking distance between the conjugated molecules. In other implementations, the solubilizing side chains are bonded to conjugated molecules and the solution is used to form the organic semiconductor film by at least one of: a branching point of the side chain to facilitate π-stacking distance between respective backbones, a crystallographic orientation between grains of the conjugated molecules, and a crystalline coherence length of in-plane π-stacking between the conjugated molecules.

Figure 1A:
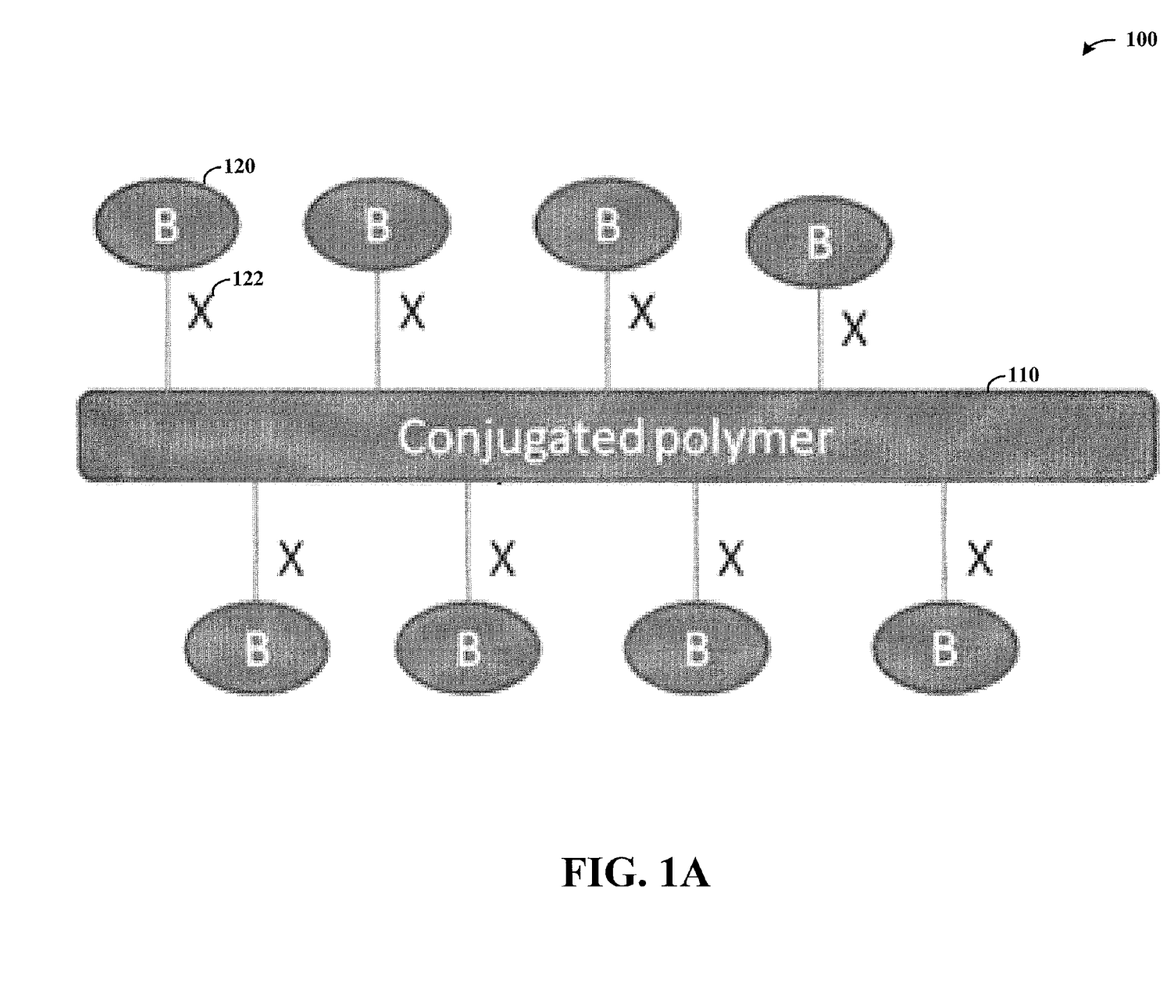
FIG. 1A shows a material including a conjugated polymer with a solubilizing side chain group, as may be implemented with various example embodiments.

Turning now to the figures, FIG. 1A shows a material 100 including a conjugated polymer backbone 110 with solubilizing side chain groups (B), as may be implemented with various example embodiments. Referring to side chain group 120 by way of example, each side chain group includes a component X (122), with the respective side chain groups (120) facilitating solubility of the conjugated polymer backbone 110 (e.g., as discussed herein).

In connection with various embodiments, component X (122) is a linear molecule having a length set based upon the size of component B (120). In some implementations, characteristics of component X are set relative to the size of component B, to facilitate close π-π stacking distances between respective conjugated polymers (e.g., with the material 100 being applied from solution into a stacked layer thereof). Accordingly, a ratio between X and B may be varied to suit particular embodiments, may be random in some embodiments, or based upon a backbone conjugated molecule that is used for other embodiments.

Figure 1B:
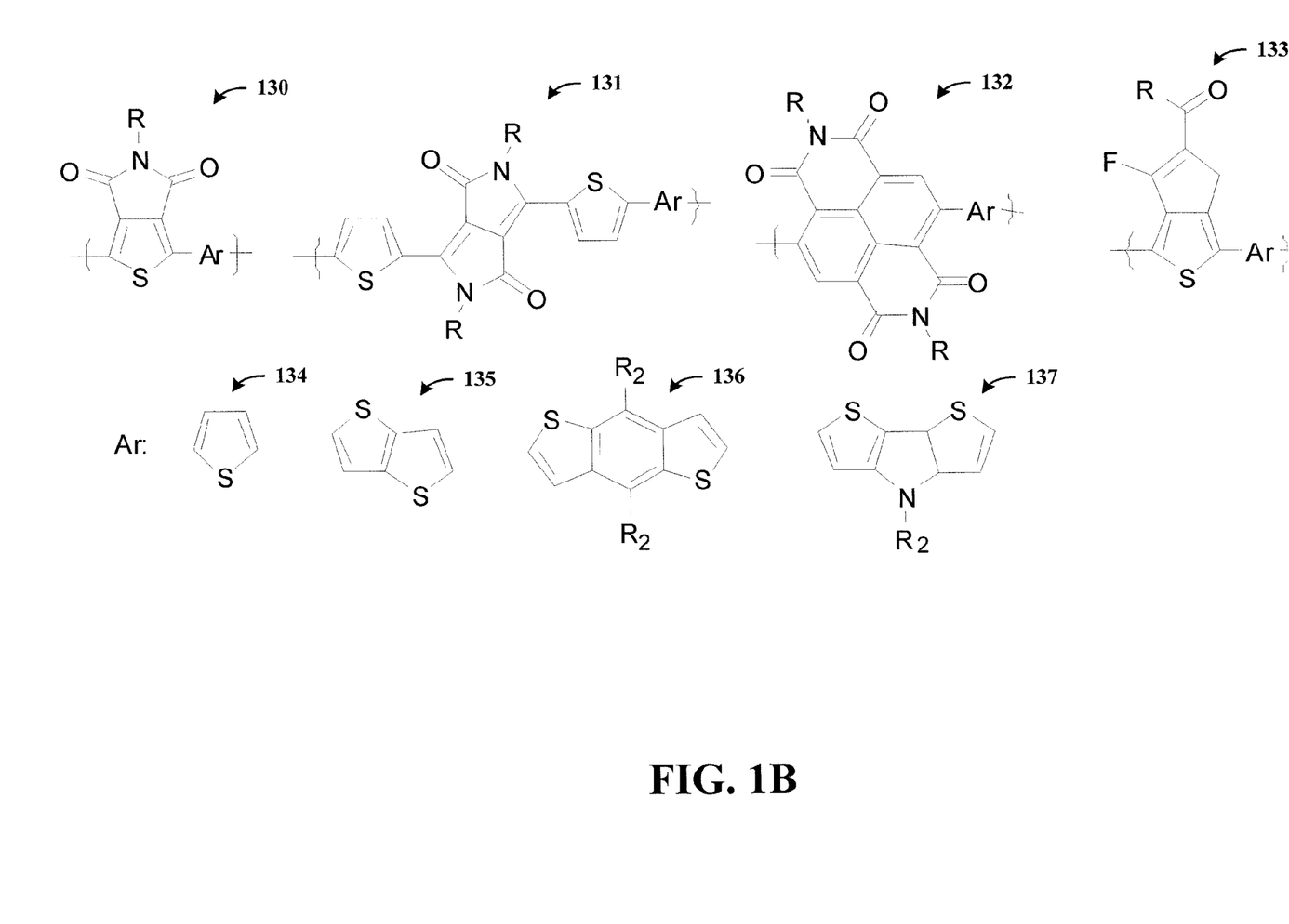
FIG. 1B shows polymer backbones, as may be implemented with one or more example embodiments.
Figure 1C:
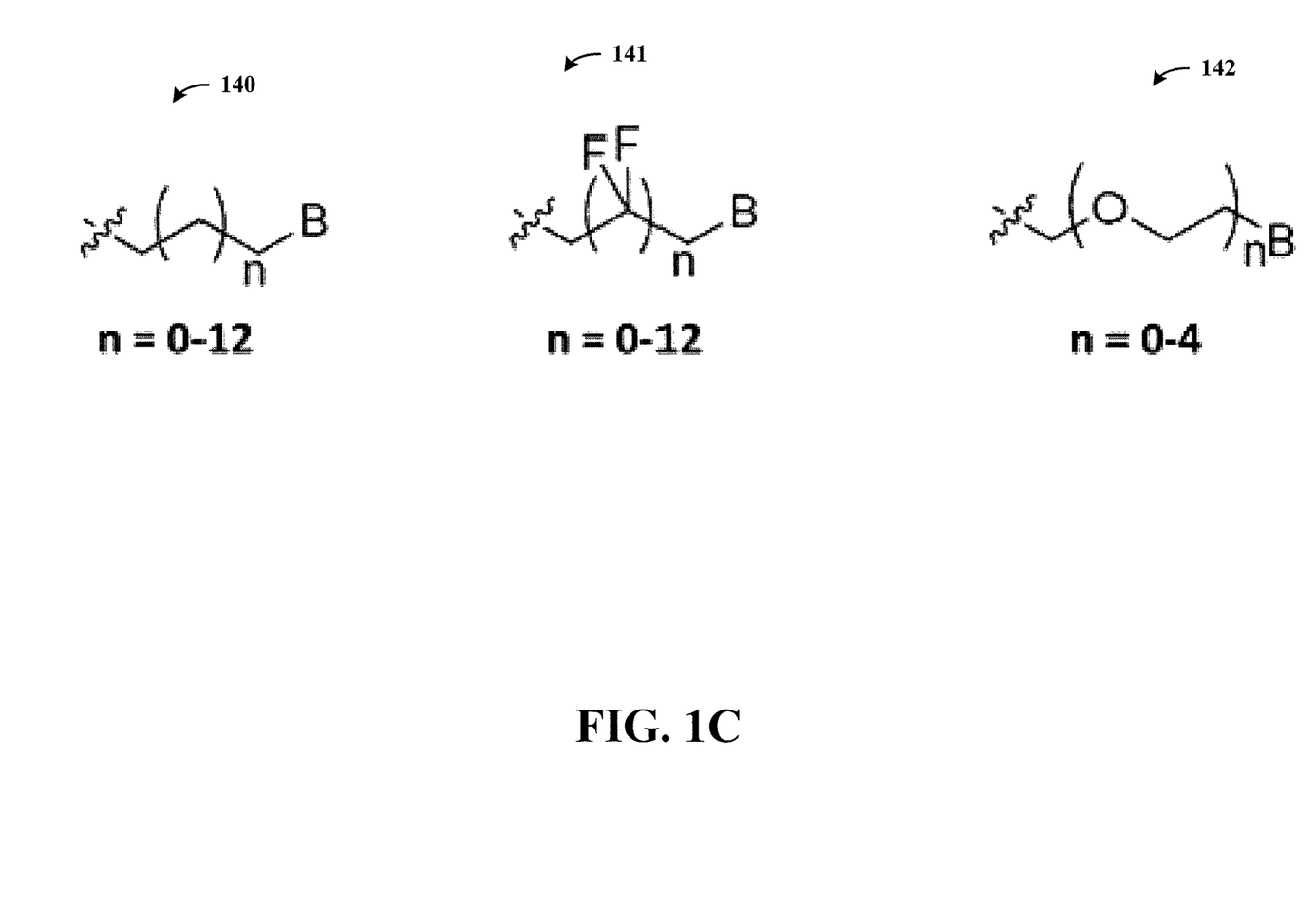
FIG. 1C shows compounds as may be implemented in connection with a solubilizing side chain, in accordance with one or more example embodiments.
Figure 1D:
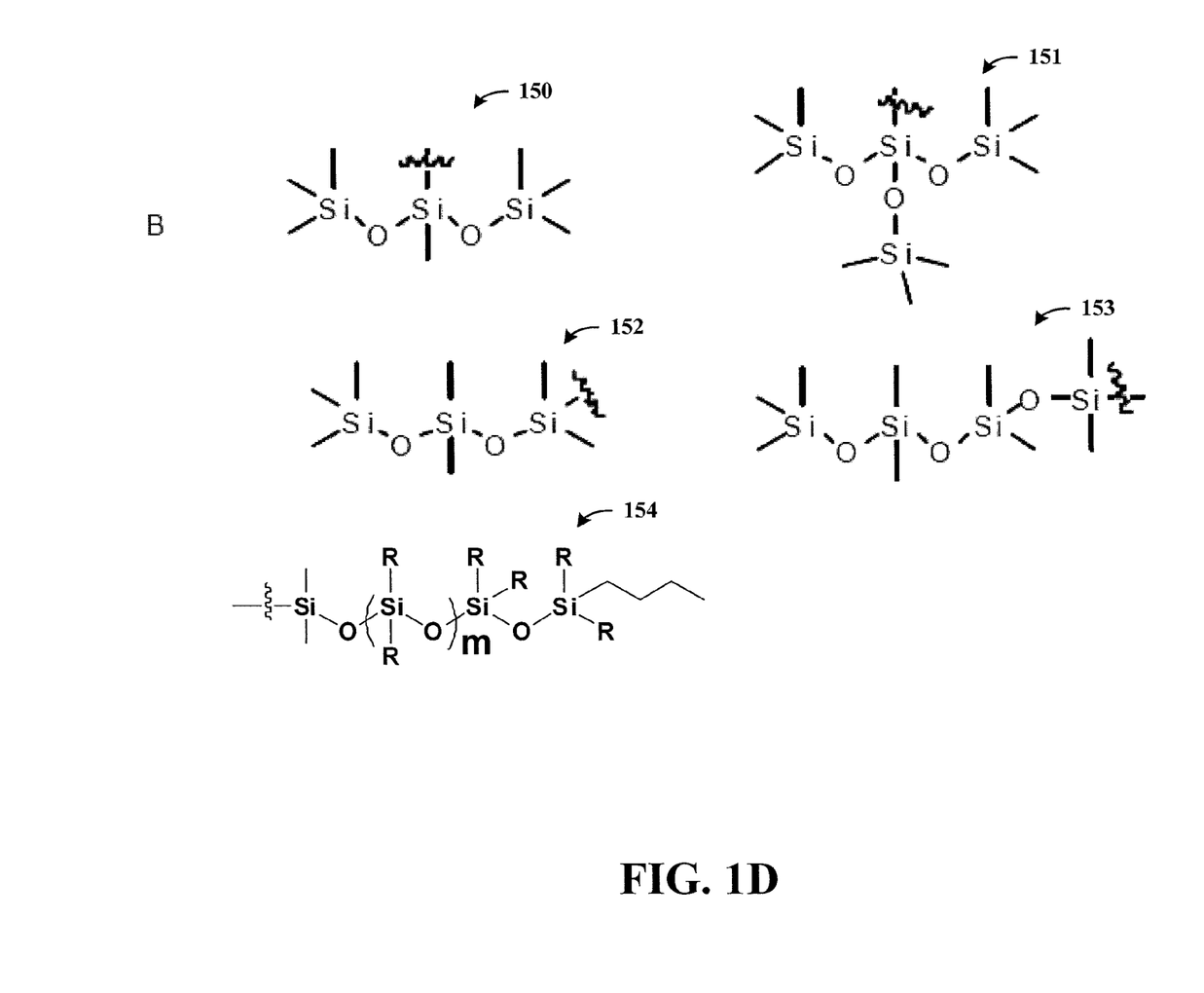
FIG. 1D shows solubilizing sidechains, as may be implemented in connection with a conjugated molecule in accordance with one or more embodiments.

FIGS. 1B-1D show materials as may be implemented (separately or combined) in connection with the structure 100 shown in FIG. 1A and/or in connection with one or more embodiments as described herein. FIG. 1B shows backbone materials 130-137, as may be implemented in connection with the conjugated polymer 110 as shown in FIG. 1A and/or in connection with one or more example embodiments as described herein. "R" is a linear aliphatic chain, such as shown in FIG. 1C, and "$R_2$" includes "R" and/or a different linear aliphatic chain.

FIG. 1C shows compounds 140-142 as may be implemented in connection with a solubilizing side chain, such as with component 122 ("X") as shown in FIG. 1A, in accordance with one or more example embodiments. "B" is a siloxane chain, such as shown in FIG. 1D. In some implementations, the value "n" in the examples for component X shown in FIG. 1C is increased as the size of component B increases to suit particular embodiments and facilitate close π-π stacking distances. Various other types of components "X" may be implemented, such as with linear siloxanes.

FIG. 1D shows solubilizing side chains 150-154, as may be implemented in connection with a conjugated molecule such as with component 120 ("B") in FIG. 1A, or with one or more embodiments as described herein. Referring to side chain 154, component "R" is implemented as one or more of a methyl, ethyl or phenyl component. In addition, the side chain as denoted "m" may be implemented with multiple such chains (e.g., 1-200).

Figure 2:
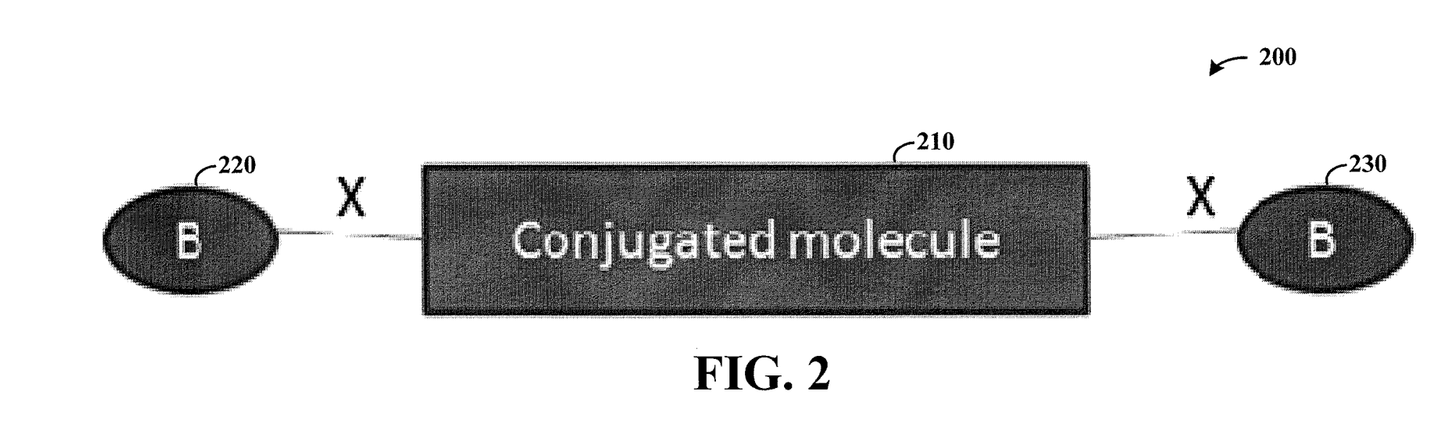
FIG. 2 shows a structure including a conjugated molecule coupled to a side chain, consistent with one or more embodiments.
Figure 3:
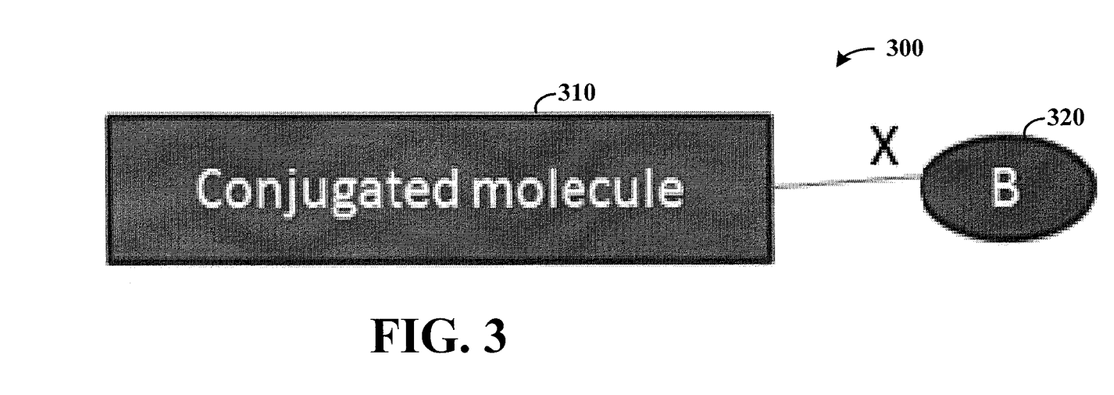
FIG. 3 shows a structure including a conjugated molecule coupled to side chains, consistent with one or more embodiments.

FIGS. 2 and 3 show structures including a conjugated molecule coupled to one or more side chains at an end(s) of the conjugated molecule. Specifically, FIG. 2 shows a structure 200 including a conjugated molecule 210 coupled to side chains 220 and 230, and which may be implemented in a manner consistent with one or more aspects described above. FIG. 3 shows a structure 300 including a conjugated molecule 310 coupled to a side chain 320, and which may be implemented in a manner consistent with one or more aspects described above.

Figure 4:
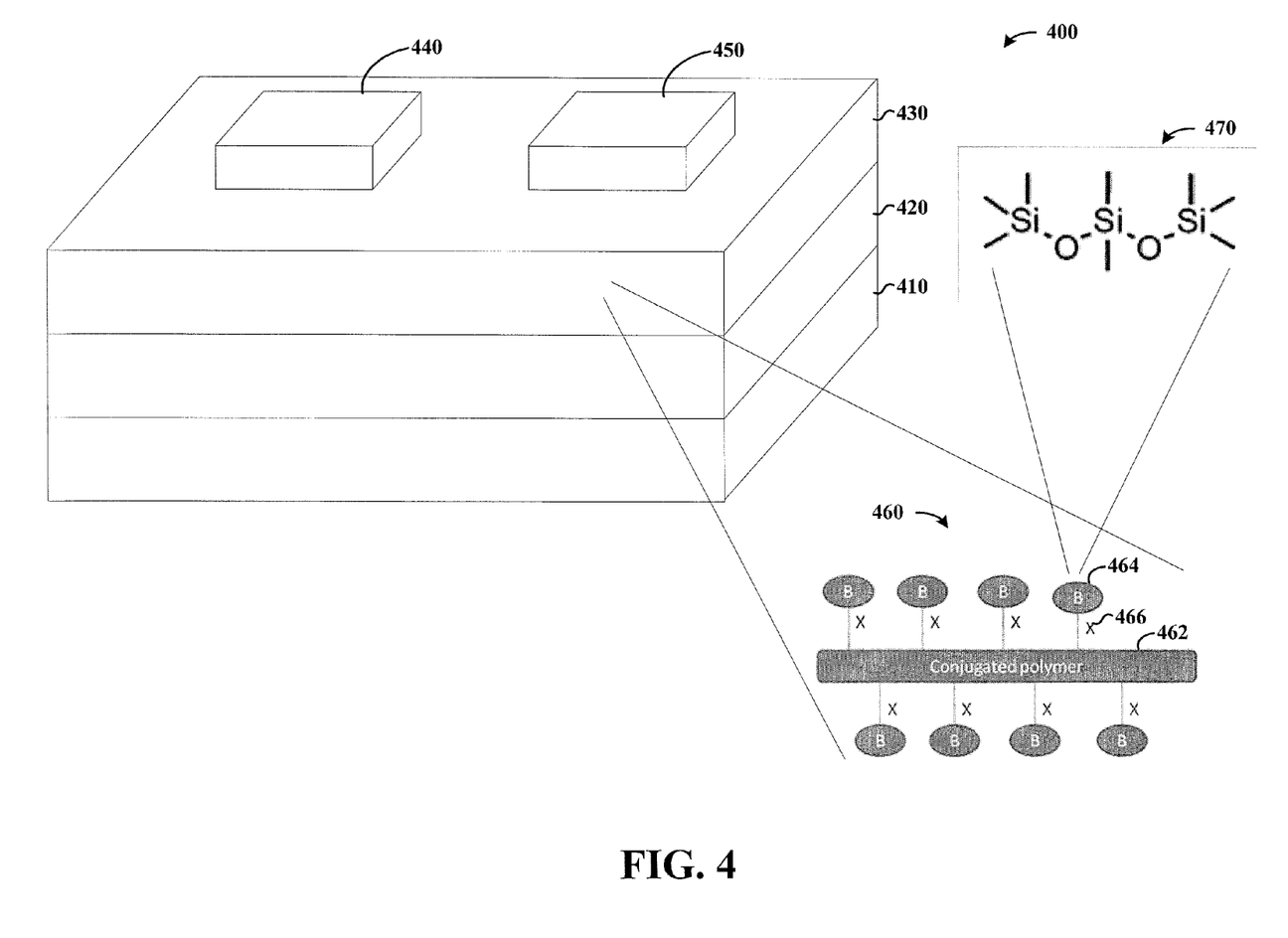
FIG. 4 shows a semiconductor apparatus 400, in accordance with another example embodiment.

FIG. 4 shows a semiconductor apparatus 400, in accordance with another example embodiment. The apparatus 400 includes a silicon-based material 410, such as $SiO_2/n^{++}$ Si, a self-assembled monolayer (SAM) 420 of octadecyltrimethoxysilane (OTMS), and a polymer layer 430 including a conjugated polymer with solubilizing sidechain as discussed in one or more embodiments herein. The apparatus 400 further includes source/drain regions 440 and 450. By way of example, an individual molecule 460 of the polymer layer 430 is shown, having a conjugated polymer backbone 462, a sidechain including material 464 (B) and 466 (x). Such an apparatus 400 may be implemented, for example, as a thin film transistor, with a channel region in the polymer layer 430 and using the closely-stacked polymer with desirable mobility therein.

While the present disclosure, including the underlying provisional patent application to which benefit is claimed, is amenable to various modifications and alternative forms, specifics thereof have been shown by way of example in the drawings and will be described in further detail. It should be understood that the intention is not to limit the disclosure to the particular embodiments and/or applications described. For instance, various materials, apparatuses and methods as described in connection with a polymer can be implemented with oligomers (and/or the term oligomer may refer to a type of polymer with a limited number of monomers). Various embodiments described above and shown in the figures and the above-referenced provisional patent application may be implemented together and/or in other manners. One or more of the items depicted in the drawings/figures, and cited references can also be implemented in a more separated or integrated manner, as is useful in accordance with particular applications.

What is claimed is:

1. A material comprising:
   conjugated molecules; and
   for each conjugated molecule, a side chain bonded to the conjugated molecule and configured and arranged to enhance solubility of the conjugated molecule, the side chain including:
   a siloxane-terminated unit; and
   a linear spacer configured and arranged to couple the siloxane-terminated unit to the conjugated molecule and to set a π-stacking distance between the conjugated molecules that facilitates carrier mobility between the conjugated molecules.

2. The material of claim 1, wherein the conjugated molecules are stacked in an organic semiconductor film having a carrier mobility set via the π-stacking distance.

3. The material of claim 1, wherein the side chain is configured and arranged to couple to the conjugated molecules to facilitate a π-stacking distance between the conjugated molecules that is shorter than a π-stacking distance of at least one of 1-ethylhexyl and 1-hexyldecyl.

4. The material of claim 1, wherein the side chain is configured and arranged to couple to the conjugated molecules to facilitate a π-stacking distance between the conjugated molecules that is less than 3.7 Angstroms.

5. The material of claim 1, wherein the side chain is configured and arranged to interact with the conjugated molecule to provide a backbone having a carrier mobility of one of at least $0.5\ cm^2V^{-1}s^{-1}$, and at least $2.00\ cm^2V^{-1}s^{-1}$.

6. The material of claim 1, wherein the side chain is configured and arranged to crosslink to form a film including the conjugated molecule.

7. The material of claim 1, wherein the conjugated molecule includes at least one of a conjugated polymer and a conjugated oligomer.

8. The material of claim 1, further including a solvent, wherein the conjugated molecule and the side chain are in solution in the solvent.

9. An apparatus comprising:
   first and second conductive terminals; and
   an organic semiconductor film electrically coupled to pass carriers between the conductive terminals and including
   a plurality of conjugated molecules, and
   for each of the conjugated molecules, a side chain bonded to the conjugated molecule configured and arranged to enhance solubility of the conjugated molecule, the side chain having a siloxane-terminated unit and a linear spacer configured and arranged to set a π-stacking distance between the conjugated molecules in the organic semiconductor film, thereby facilitating carrier mobility between the conjugated molecules.

10. The apparatus of claim 9, wherein the linear spacer is bonded to the conjugated molecule and configured and arranged with bond angles and a branch site offset of the side chain that set the π-stacking distance between the conjugated molecules.

11. The apparatus of claim 10, wherein the π-stacking distance between the conjugated molecules is less than 3.6 Angstroms.

12. The apparatus of claim 9, wherein the conjugated molecules include at least one of a conjugated polymer and a conjugated oligomer.

13. The apparatus of claim 9, wherein the side chain is configured and arranged to interact with the conjugated molecule to provide a carrier mobility in the organic semiconductor film of one of: at least $0.5\ cm^2V^{-1}s^{-1}$, and at least $2.00\ cm^2V^{-1}s^{-1}$.

14. The apparatus of claim 9, wherein the side chain and the conjugated molecules are configured and arranged with a relative π-stacking distance, crystallographic orientation and crystalline coherence length that provide a carrier mobility within the organic semiconductor film of at least $2\ cm^2V^{-1}s^{-1}$.

15. A material comprising a solubilizing side chain including a linear chain and a siloxane-terminated unit including:

wherein the linear chain is configured and arranged with the siloxane-terminated unit to couple the siloxane-terminated unit to a conjugated molecule backbone and to set a π-stacking distance between the siloxane-terminated unit and the conjugated molecule backbone.

16. The material of claim 15, wherein the siloxane-terminated unit includes at least one of the following structures:

m = 1-200

17. The material of claim 15, wherein the linear chain includes at least one of the following structures in which "B" is a siloxane chain:

n = 0-12     n = 0-12 n = 0-4

18. The material of claim 17, further comprising at least one of the following structures bonded to the siloxane-terminated unit, in which "R" is a linear aliphatic chain, "$R_2$" includes at least one of "R" and a linear aliphatic chain that is different than "R," and X includes one of O, S and Se:

19. A method comprising:
bonding solubilizing side chains to conjugated molecules, each side chain including a siloxane-terminated unit and a linear spacer, the linear spacer configured and arranged to set a π-stacking distance between the conjugated molecules that facilitates carrier mobility between the conjugated molecules; and
forming a solution in a solvent by using the solubilizing side chains to increase solubility of the conjugated molecules in the solvent.

20. The method of claim 19, further including using the solution to form an organic semiconductor film of the conjugated molecules having the solubilizing side chains bonded thereto, while using the solubilizing side chains to set a π-stacking distance between the conjugated molecules that facilitates carrier mobility between the conjugated molecules in the organic semiconductor film.

21. The method of claim 20, wherein each side chain includes the linear spacer that is bonded to the conjugated molecule and that is configured and arranged with bond angles and a branch site offset that set the π-stacking distance between the conjugated molecules.

22. The method of claim 20, wherein bonding solubilizing side chains to conjugated molecules and using the solution to form the organic semiconductor film include setting at least one of: a branching point of the side chain to facilitate π-stacking distance between respective backbones, a crystallographic orientation between grains of the conjugated molecules, and a crystalline coherence length of in-plane π-stacking between the conjugated molecules.

* * * * *